United States Patent [19]

Shigeyasu et al.

[11] 4,370,496

[45] Jan. 25, 1983

[54] PROCESS FOR CONTINUOUS PRODUCTION OF HIGH PURITY TEREPHTHALIC ACID

[75] Inventors: Motoo Shigeyasu; Michio Kuki, both of Matsuyama, Japan

[73] Assignee: Matsuyama Petrochemicals Inc., Osaka, Japan

[21] Appl. No.: 953,321

[22] Filed: Oct. 20, 1978

Related U.S. Application Data

[63] Continuation of Ser. No. 671,929, Mar. 31, 1976, abandoned.

[30] Foreign Application Priority Data

Dec. 25, 1975 [JP] Japan ............................ 50-155553

[51] Int. Cl.³ ...................... C07C 51/42; C07C 51/16
[52] U.S. Cl. .................................. 562/487; 562/412; 562/416
[58] Field of Search ...................... 562/412, 487, 416

[56] References Cited

U.S. PATENT DOCUMENTS 3,859,344  1/1975  Shigeyasu et al. ............... 562/412

*Primary Examiner*—Alan Siegel
*Attorney, Agent, or Firm*—Sughrue, Mion, Zinn, Macpeak & Seas

[57] ABSTRACT

A process for continuously producing high purity terephthalic acid, in particular, useful for direct polymerization, which comprises continuously introducing p-dialkylbenzene as a feed material together with a solvent and an oxidation catalyst into a reactor, subjecting the p-dialkylbenzene to a liquid phase oxidation with oxygen in the reactor to produce terephthalic acid, continuously or intermittently introducing the reaction mixture containing terephthalic acid thus produced into a stabilizer, and oxidizing the reaction mixture in the stabilizer for an extended period of time with a molecular oxygen containing gas of a low oxygen concentration at a temperature and pressure the same as or lower than those in the oxidation reaction while keeping the volume change of the contents in the stabilizer below about 30% by volume of the contents of the stabilizer.

17 Claims, 1 Drawing Figure

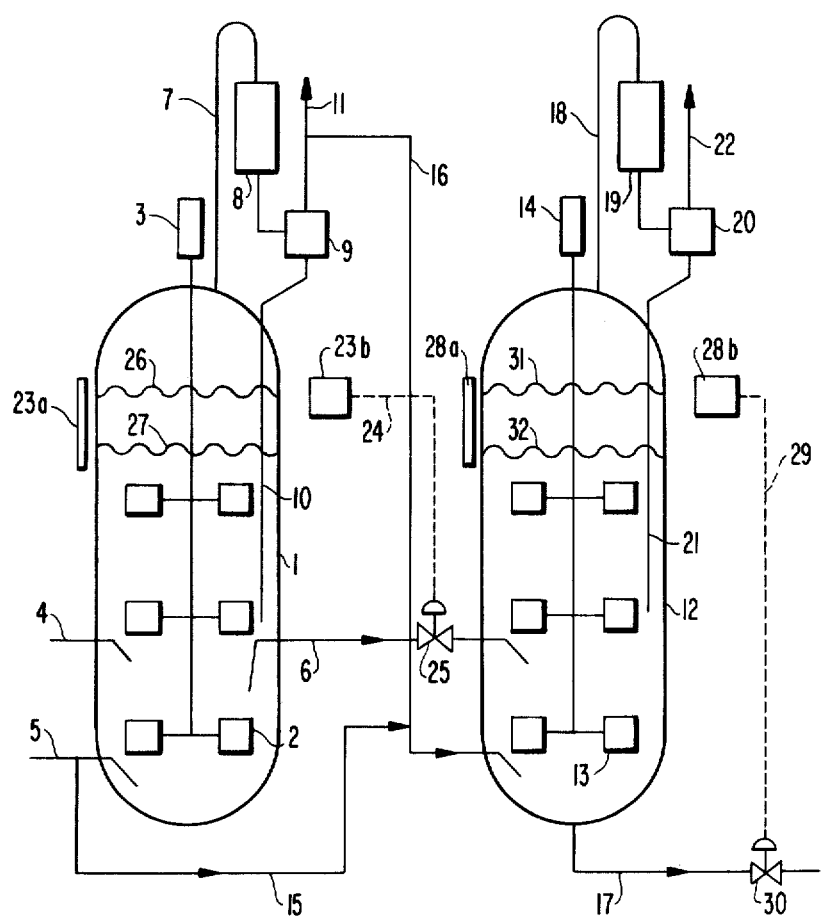

PROCESS FOR CONTINUOUS PRODUCTION OF HIGH PURITY TEREPHTHALIC ACID

This is a continuation of application Ser. No. 671,929, filed Mar. 31, 1976, now abandoned.

BACKGROUND OF THE INVENTION

1. Field of the Invention

The present invention relates to a process for producing high purity terephthalic acid by the liquid phase oxidation of a p-dialkylbenzene such as p-xylene, more particularly, to a process of producing high purity terephthalic acid by introducing a reaction mixture containing terephthalic acid formed by continuous oxidation to a vessel other than the oxidation reactor and treating the reaction mixture therein for an extended period of time with a molecular oxygen containing gas having a low oxygen concentration.

2. Description of the Prior Art

Various processes have hitherto been proposed for producing terephthalic acid by subjecting a p-dialkylbenzene such as p-xylene to a liquid phase oxidation with molecular oxygen in the presence of a solvent such as acetic acid and an oxidation catalyst. These prior art processes are generally classified into the following groups according to the reaction mode.

One group relates to a batch system wherein the total amount of feed dialkylbenzene, solvent and catalyst is charged into a reactor prior to reaction, an oxygen containing gas is then introduced and, after the reaction is completed, the total amount of the reaction mixture is discharged from the reactor.

Another group involves a semi-continuous system wherein a feed dialkylbenzene (in some cases, together with a part of the solvent and catalyst to be used) and an oxygen containing gas are continuously introduced into a reactor containing all or the balance of the solvent and catalyst, and, after the reaction is completed, the total amount of the reaction mixture is discharged from the reactor.

The last group relates to a continuous system wherein a feed dialkylbenzene and an oxygen containing gas are continuously introduced into a reactor together with a solvent and a catalyst and then the reaction mixture is continuously or intermittently discharged from the bottom of the reactor.

Among these systems, the present invention is particularly directed to an improvement of the continuous system.

Recently, a direct polymerization process for producing a polyester from terephthalic acid by directly polymerizing high purity terephthalic acid and ethylene glycol or ethylene oxide was developed. This polymerization process is economically very advantageous over conventional processes where terephthalic acid is polymerized after it has once been esterified into dimethyl terephthalic which can be purified more easily than terephthalic acid. However, in direct polymerization high quality terephthalic acid is required as a raw material. Also, the direct production of terephthalic acid by a continuous system has high industrial advantage since the process can be performed in a simplified manner, terephthalic acid having constant quality can be produced in a stable fashion for long periods of time, and, further, the yield of product per unit volume of the reactor and per unit time is better than in the batch system and the semi-continuous system.

However, direct continuous processing has the demerit that since the amount of the reaction material discharged from the reactor without being contained a sufficient retention time in the reactor is larger than in the batch system and the semi-continuous system, the quality of the terephthalic acid produced is insufficient due to the increased contents of unreacted feed material and reaction intermediate product, e.g., reaction intermediate products such as 4-carboxybenzaldehyde, p-toluic acid, etc., and, though in very slight amounts, very active compounds in addition to terephthalic acid. If oxidizable materials such as these reaction intermediate products and active compounds are not rapidly oxidized to be converted into terephthalic acid or non-toxic materials (in this invention the reaction of completing the oxidation is called "stabilization" and the reaction vessel for performing the stabilization is called a "stabilizer"), they are converted into side reaction products such as fluorenone, diketones, etc., which reduce the quality, in particular, the color hue, of the product terephthalic acid.

Therefore, an improvement has been proposed wherein high purity terephthalic acid is obtained by completing the oxidation of the reaction intermediate products and the active materials contained in the reaction mixture after the oxidation reaction is completed. For example, Japanese Patent Publication No. 12,695/'65 discloses a process of producing high purity terephthalic acid by subjecting a reaction mixture containing terephthalic acid to further oxidation with air for about one hour at temperatures (200° to 300° C.) higher than the temperature in the liquid phase oxidation of p-dialkylbenzene after the oxidation reaction is completed. However, although this process is efficient in achieving complete oxidation, it is accompanied by disadvantages such as the reaction product is unavoidably colored because of the formation of by-products due to the additional treatment with oxygen at higher temperatures after the oxidation reaction is completed, and, further, there is the possibility of explosion due to the increase in the concentration of oxygen in the reaction system which may exceed the explosive limit (8% by volume oxygen concentration in the gas phase) due to the continuous introduction of air into the system over an extended period of time.

To improve the disadvantages in conventional oxidation processes, the inventors previously discovered a process of producing high purity terephthalic acid of good color hue continuously as described in U.S. Pat. No. 3,859,344 wherein a p-dialkylbenzene is continuously subjected to a liquid phase oxidation with molecular oxygen in the presence of a solvent and an oxidation catalyst in a reaction vessel, the oxidation reaction product obtained is partially discharged from the reaction vessel and introduced into a small size stabilizer having such a capacity that the amount of the discharged reaction product each time occupies 30 to 70% by volume of the contents of the stabilizer, and then the reaction product is further subjected to an oxidation treatment with air for 1 to 5 minutes at a temperature the same as or lower than that in the preceding oxidation reaction in such a range that the oxygen content in the reaction system does not exceed the explosive limit. That is, to perform the complete stabilization of the materials to be oxidized in the reaction product discharged in an oxidation reaction vessel, it is required to sufficiently contact the materials with air, but when an oxygen containing gas having a high oxygen content such as air is used for this purpose, the oxygen content in the stabilizer may exceed the explosive limit to give a possibility of explosion.

Thus, based on the discovery that it is necessary to not reduce the concentration of the materials to be oxidized in the reaction mixture to effectively perform the stabilization within an oxygen content range not exceeding the explosive limit, the inventors previously established the process of the aforesaid U.S. patent in which the reaction mixture containing the products is partially introduced into a small size stabilizer in an amount of 30 to 70% by volume of the contents of the stabilizer to bring the reaction mixture into contact with air for a short period of time (1 to 5 minutes) in the stabilizer, and then the greater part of the reaction mixture is immediately discharged from the stabilizer to repeat the same step.

According to the process of this U.S. patent, stabilization can be effectively achieved with an oxygen content in the stabilizer which does not exceed the explosive limit. However, in the process it is required to frequently repeat the steps of discharging the reaction mixture intermittently in a constant amount from an oxidation reaction vessel, introducing the reaction mixture into a small size stabilizer, bringing it into contact with air for 1 to 5 minutes with an oxygen content in the system which does not exceed the explosive limit, stopping the introduction of air, and discharging the greater part of the reaction mixture in the stabilizer. Thus, the process is complicated. In particular, since in this process the temperature and the pressure in the stabilizer change greatly due to the large volume change of the contents of the stabilizer, which makes it difficult to control the temperature and the pressure, and also the composition of the contents of the stabilizer changes frequently and periodically, the merits of continuously producing products of constant quality over a long period of time in a stable manner is not effectively utilized. Furthermore, in this process the introduction of the oxygen containing gas is temporarily stopped, which results in readily causing precipitation of the product at the bottom of the stabilizer, etc.

Therefore, it is most desirable to establish a continuous process of producing terephthalic acid of constant high quality for extended periods of time by effectively achieving stabilization with an oxygen content in the reaction system which does not exceed the explosive limit while introducing an oxygen containing gas continuously into the stabilizer without interrupting the introduction of the gas.

SUMMARY OF THE INVENTION

As a result of extensive and elaborate research to further improve the process of U.S. Pat. No. 3,859,344 described above, the inventors discovered that in a process of continuously producing terephthalic acid by subjecting a p-dialkylbenzene to a liquid phase oxidation with molecular oxygen in the presence of a heavy metal containing oxidation catalyst and a lower aliphatic carboxylic acid as a solvent, high purity terephthalic acid of constant quality can be continuously produced at high yield by introducing the reaction mixture containing terephthalic acid obtained into a stabilizer, bringing the reaction mixture into contact with a molecular oxygen containing gas having an oxygen content lower than that of air for extended periods of time with an oxygen content in the gaseous phase in the stabilizer which does not exceed the explosive limit at a temperature and pressure the same as or lower than those in the oxidation reaction, and withdrawing the reaction mixture from the stabilizer, the introduction and withdrawal of the reaction mixture being so performed that the volume change of the contents in the stabilizer is kept below about 30% by volume of contents of the stabilizer, whereby the stabilization of the materials to be oxidized contained in the reaction mixture is efficiently completed.

An object of this invention is, therefore, to provide a process of continuously producing high purity terephthalic acid with stable operation for extended periods of time.

Another object of this invention is to provide a process of continuously producing high purity terephthalic acid of constant quality by treating a reaction mixture containing terephthalic acid obtained by a continuous oxidation with an oxygen containing gas of low oxygen content for extended periods of time in a stabilizer while reducing the volume change of the contents of the stabilizer.

Still yet another object of this invention is to provide a process of directly producing by only an oxidation reaction step fiber grade terephthalic acid suitable for the raw material in a direct polymerization reaction in which high quality polyester for manufacturing fibers is produced by directly reacting terephthalic acid and ethylene glycol or ethylene oxide without the need of any additional purification treatments.

Other objects and advantages of this invention will become apparent by the following detailed description.

BRIEF EXPLANATION OF THE DRAWING

FIG. 1 is a flow sheet illustrating one embodiment of the process of this invention.

DESCRIPTION OF THE PREFERRED EMBODIMENTS

According to the present invention, there is provided a process of continuously producing high purity terephthalic acid by continuously introducing a p-dialkylbenzene into an oxidation reactor together with a solvent and an oxidation catalyst, oxidizing the p-dialkylbenzene in the liquid phase with molecular oxygen or a molecular oxygen containing gas, and separating and recovering the terephthalic acid thus formed from the reaction mixture by crystallization, which comprises introducing the oxidation product from the oxidation reactor into a stabilizer and oxidizing the oxidation reaction product for from about 5 to about 300 minutes at a temperature and a pressure the same as or lower than those employed in the preceding oxidation reaction, by continuously introducing a molecular oxygen containing gas having an oxygen concentration lower than that of air so that the oxygen concentration in the stabilizer does not exceed the explosive limits thereof during the treatment and while maintaining the volume change of the contents of the stabilizer below about 30% by volume of the contents of the stabilizer.

In the process of our aforesaid U.S. Pat. No. 3,859,344, the oxidation reaction product is treated with a gas having a high oxygen concentration, such as air, for a short period of 1 to 5 minutes in a stabilizer, the volume deviation of the contents of the stabilizer is as large as 30 to 70% by volume, and, further, the gas having a high oxygen concentration is introduced intermittently into the stabilizer. On the other hand, in the process of the present invention, the oxidation reaction product is treated with a gas having an oxygen concentration lower than that of air in a stabilizer by continuously (without intermission) introducing the oxygen containing gas into the system for about 5 to about 300 minutes and the volume change of contents of the stabilizer is kept as low as below about 30% by volume.

As compared with the conventional process of producing terephthalic acid in which the steps of intermittent introduction of an oxygen containing gas to the stabilizer and withdrawing the greater part of the reaction product in the stabilizer are applied intermittently at high frequency, the process of this invention has the advantages that the stabilization can be performed effectively and continuously at a low volume change of the contents of the stabilizer while continuously introducing an oxygen containing gas to the reaction system without intermittent introduction of the gas and in an oxygen concentration range which does not exceed the explosive limit, which results in continuously producing high quality terephthalic acid of constant properties for extended periods of time by a stable operation.

The inventors also attempted to retain large contents of reaction product in a large sized stabilizer for continuously introducing (without intermission) an oxygen containing gas having a high oxygen concentration, such as air, into the stabilizer and then withdrawing the contents therefrom while maintaining the volume deviation of the contents at a low level, but failed to obtain good stabilization. This is based on the following reason. That is, since a large amount of oxidation reaction product which has already undergone stabilization is present in such a stabilizer, the materials to be oxidized by the stabilization in the stabilizer are greatly reduced in concentration due to the presence of the high amounts of the aforesaid stabilized oxidation reaction product. To perform stabilization of the materials to be oxidized by introducing an oxygen containing gas having a high oxygen concentration, such as air, into the reaction system, the amount of air introduced into the system must be low due to the requirement of keeping the oxygen concentration in the reaction system below the explosive limits (i.e., due to the requirement of avoiding the occurrence of explosion). When such a small amount of air is introduced into the stabilizer containing these materials, the gas-liquid contact becomes insufficient, i.e., air is dispersed in such a large volume of the contents in the stabilizer that the amount of oxygen present throughout the total reaction system becomes deficient, which makes it difficult to achieve a quick, effective stabilization of the materials to be oxidized, which are present in the reaction system at a low concentration.

If, on the other hand, an increased amount of air is introduced into the reaction system to increase the stabilization effect, the oxygen concentration in the system (i.e., the gaseous phase portion in the stabilizer) immediately increases beyond the explosive limit to cause the danger of explosion, which makes the industrial practice of the stabilization treatment impossible.

According to the process of this invention, a large amount of an oxygen containing gas having a low oxygen concentration can be blown into a stabilizer without increasing the oxygen concentration in the stabilizer beyond the explosive limit, and, hence, oxygen can be effectively distributed throughout the total reaction system in the stabilizer to perform a uniform, quick gas-liquid contact in the stabilizer in spite of the fact that the materials to be oxidized are in a diluted state as described above, which results in an effective stabilization, i.e., a quick conversion of the materials to be oxidized such as reaction intermediate products and active compounds into terephthalic acid and other harmless materials. Furthermore, since a large amount of a low oxygen concentration gas is introduced into the bottom of the stabilizer in the process of this invention, the stirring effect in the stabilizer is increased to prevent crystals of terephthalic acid formed from being deposited or accumulated on the bottom of the stabilizer or the conduit for withdrawing the reaction product from the stabilizer from being clogged by deposits.

It should be noted, in this regard, that it is not mandatory to introduce the oxygen containing gas only into the bottom of the stabilizer, though for purposes of increasing the retention time of the oxygen, and effecting good stirring at the bottom of the stabilizer, the oxygen containing gas as a matter of practice is at least partially introduced into the bottom of the stabilizer. It is possible, of course, to introduce the oxygen containing gas into the bottom and the middle of the stabilizer separately, if desired; of course, in this case, it is practically necessary to introduce a large proportion of the gas into the bottom of the stabilizer to achieve the above increased retention time and stirring effects. Suffice it to say, that for most preferred commercial operation introduction of the oxygen containing gas to the bottom and, if desired other portion(s) of the stabilizer is utilized.

The process of this invention can be applied to any process for continuously producing terephthalic acid by the liquid phase oxidation of p-dialkylbenzene, but is particularly effectively applied to the production of fiber grade terephthalic acid which can be used in the direct polymerization reaction of preparing high quality polyesters by reaction with ethylene glycol or ethylene oxide.

The liquid phase oxidation of dialkylbenzene in this invention may be carried out in a conventional manner, but is preferably carried out under the following reaction conditions.

The reaction temperature is generally about 80° to about 250° C., preferably 130° to 220° C. Since the reaction is carried out in the liquid phase, it is necessary to carry out the reaction under a pressure so as to maintain the raw material, p-dialkylbenzene, and the solvent in the liquid phase at the reaction temperature. A preferred pressure range for the reaction is about 2 to about 30 kg/cm$^2$ gauge. The mean retention time of the reactants in the oxidation reactor is about 0.5 to about 6 hours, preferably 1 to 3 hours.

The starting material is a p-dialkylbenzene, in which any alkyl moiety preferably is a $C_1$–$C_3$ alkyl group, e.g., such as p-xylene, p-diisopropylbenzene, p-cymene, p-diethylbenzene, etc., but the use of p-xylene is most preferred. Also, a lower aliphatic carboxylic acid, in which the aliphatic moiety preferably has 1 to 3 carbon atoms, e.g., such as acetic acid, propionic acid, butyric acid, etc., is used as a solvent, but the use of acetic acid is particularly preferred. The amount of the solvent used is usually more than about twice by weight the amount of the feed dialkylbenzene, but it is preferred to use the solvent in an amount of 3 to 6 times the weight of the feed dialkylbenzene.

In the liquid phase oxidation reaction, molecular oxygen or a molecular oxygen containing gas is used as the oxidizing agent, but air is most advantageously used. The proportion of oxygen employed depends upon the kind of the p-dialkylbenzene used as the raw material, but when, for example, p-xylene is used as the raw material, the amount of oxygen is usually about 2 to about 500 moles, preferably 3 to 300 moles, per mole of p-xylene.

Furthermore, as the oxidation catalyst in the liquid phase oxidation, a heavy metal compound such as a cobalt and manganese compound, or a bromine compound is used. In general, a heavy metal compound is used in combination with a bromine compound. Preferred examples of the heavy metal compound are inorganic salts, naphthenates and lower aliphatic salts of cobalt and manganese. Preferred examples of the bromine compound are inorganic bromine salts such as sodium bromide, potassium bromide, ammonium bromide, etc.; elementary bromine; hydrogen bromide; and organic bromine compounds. The amount of each of these oxidation catalysts is, in general, about 0.0001 to about 1.0% by weight, preferably 0.001 to 0.5% by weight, based on the weight of, as a solvent, the lower aliphatic carboxylic acid for the heavy metal compound (calculated as the heavy metal), and about 0.1 to about 10 times, preferably 0.5 to 6 times, the weight of the heavy metal for the bromine compound or bromine (calculated as bromine), respectively. In addition, a bromide of a heavy metal such as cobalt, manganese, etc., can be used as the oxidation catalyst having both components for the above-mentioned heavy metal compound and the bromine compound. Furthermore, it is possible in the liquid phase oxidation to use a reaction accelerator such as a ketone or aldehyde.

The reaction product obtained by the oxidation reaction in the oxidation reactor is immediately introduced into a stabilizer and oxidized with an oxygen containing gas having an oxygen concentration lower than that of air for about 5 to about 300 minutes in the stabilizer according to the process of this invention. As the low oxygen containing gas introduced into the stabilizer, an off-gas (usually containing about 0.5 to about 7% by volume unreacted molecular oxygen) discharged from an oxidation reactor in the liquid phase oxidation of p-dialkylbenzene is most advantageously used. As one skilled in the art will appreciate, the off-gas cannot be unequivocally defined since it will vary depending upon the primary reaction conditions; however, it can be said that on a commercial scale the off-gas will often comprise about 90 to about 99.5% nitrogen, about 0.5 to about 7% by weight oxygen and a trace up to about 2% carbon dioxide, with less than about 1% carbon monoxide gas being present, wherein all percents are by volume. When the stabilization in the stabilizer proceeds effectively using only the off-gas discharged from the oxidation reactor, the off-gas only may be introduced into the stabilizer. However, if necessary, the off-gas may be introduced into the stabilizer together with a high oxygen containing gas such as air to increase the stabilization effect. In this case, both gas components may be introduced as a mixture thereof having a predetermined oxygen content or may be introduced therein separately.

Furthermore, in place of the off-gas from the oxidation reactor, a gas having a reduced oxygen concentration formed by burning a fuel together with an oxygen containing gas such as air and a gas obtained by diluting an oxygen containing gas such as air with an inert gas such as nitrogen gas, etc., may be used.

The oxygen concentration in the oxygen containing gas introduced into a stabilizer depends greatly upon the content of the materials to be oxidized contained in the oxidation reaction product to be treated in the stabilization, the treatment time in the stabilization, the desired quality of the product terephthalic acid, etc., but is lower than the oxygen concentration of air and is usually about 2 to about 15% by volume, preferably 2 to 10% by volume, most preferably 2 to 7% by volume.

The amount of the gas introduced into the stabilizer depends upon the amount of the materials to be oxidized in the oxidation reaction product, the oxygen concentration of the gas, and the reaction conditions in the preceding liquid phase oxidation, such as the charging rate of the p-dialkylbenzene into the oxidation reactor, the amount of carboxylic acid solvent used, etc. The amount of the off-gas discharged from the oxidation reactor introduced into the stabilizer is usually about 0.01 to about 10,000 liters (N.T.P.), preferably 1 to 5,000 liters, per kilogram of the oxidation reaction material contained in the stabilizer. Also, as described above, if necessary, air may be used together with the off-gas and in this case the amount of air employed is less than about 2,000 liters (N.T.P.), preferably less than about 1,000 liters, per kilogram of the oxidation reaction product.

Although the above situation applies to the case when an off-gas is used, similar or equivalent amounts of oxygen are utilized when other gases are used as the source of oxygen for stabilization, for example, taking the off-gas composition as earlier given as representative, one skilled in the art can easily calculate the amount of oxygen generally utilized when other gases are utilized with other varying oxygen contents.

If the amount of the gas blown into the stabilizer increases, the distribution or dispersion of oxygen in the system becomes better to accelerate gas-liquid contact in the system, but if the amount of the gas introduced is larger than the necessary amount, the temperature of the stabilization treatment is lowered to make the performance of effective stabilization difficult. On the other hand, if the amount of gas introduced is too low, sufficient stabilization is not obtained. In addition, the oxygen concentration in the stabilizer (gaseous phase) is preferably as high as possible in the range not exceeding the explosive limit and is preferably 2 to 7% by volume.

The treatment temperature in the stabilization in the process of this invention is at a temperature not higher than the oxidation reaction temperature as in the process disclosed in Japanese Patent Publication No. 12,695/'65 and is the same as or lower than the oxidation reaction temperature. The stabilization is carried out at temperatures lower than the oxidation reaction temperature by usually 0° to 100° C., preferably 0° to 60° C., most preferably 5° to 50° C. A treatment temperature higher than the oxidation reaction temperature may accelerate the oxidation of the reaction intermediate products such as 4-carboxybenzaldehyde and may be effective in this sense, but such a high temperature treatment must be avoided since in such a case the occurrence of side reaction is accelerated at the same time to greatly reduce the color hue of the terephthalic acid. On the other hand, when the treatment temperature is extremely low, the rate of the oxidation of the materials to be oxidized is reduced to make the stabilization insufficient.

The treatment pressure in the stabilization is merely that necessary to maintain the solvent present in the stabilizer in the liquid phase and may be one the same as or lower than the pressure in the aforesaid liquid phase oxidation.

In a preferred embodiment of the stabilization, the treatment temperature is about 80° to about 250° C., preferably 130° to 220° C. and the pressure is about 2 to about 30 kg/cm² gauge.

If the mean retention time of the oxidation reaction product is the stabilizer is longer than about 5 minutes, the stabilization effect becomes higher, but in order to prolong the retention time, it is necessary to increase the capacity of the stabilizer, and, thus, the economically preferred retention time is about 5 to about 300 minutes, particularly 10 to 200 minutes. If the mean retention time is shorter than about 5 minutes, the contact between the materials to be oxidized contained in the oxidation reaction product and oxygen is insufficient, and hence effective stabilization is not obtained.

It is most preferred in accordance with the present invention that the treating time be from 10 to 200 minutes and the volume deviation be maintained below 27% by volume.

Since in the stabilization of this invention, the oxidative treatment is performed at high temperature and high pressure, any reaction vessel equipped with a reflux condenser, a stirrer, and a capacity sufficient to maintain the aforesaid retention time may be employed for the stabilization as the oxidation reactor. Usually, it is most advantageous to use a crystallizer as is employed for crystallizing crystals of terephthalic acid in conventional processes as the stabilizer. In this case, the stabilization of the oxidation reaction product contained in the crystallizer is achieved by introducing the off-gas from the oxidation reactor together with, if necessary, air into the crystallizer at the bottom thereof. Furthermore, the stabilization reaction can be practiced in a reaction vessel other than the crystallizer. In short, the exact reaction vessel selected for the stabilization is not limited. One example of a crystallizer utilizable in the present invention is disclosed in U.S. Pat. No. 3,170,768.

In the process of this invention, it is important to maintain the volume change of the contents of the stabilizer during the progress of the stabilization below about 30% by volume. If the volume change of the contents of the stabilizer is larger than about 30% by volume of the contents of the stabilizer, the volume and composition of the contents or reaction system in the stabilizer greatly change to make it quite difficult to control the temperature and the pressure in the stabilizer, and, hence, it becomes difficult to continuously produce high purity terephthalic acid having constant quality for long periods of time.

To perform the stabilization while maintaining the volume change of the contents of the stabilizer below about 30% by volume, the amount of the oxidation reaction product introduced into the stabilizer and the amount of the reaction product withdrawn from the stabilizer may be controlled. Any process and/or means capable of controlling these amounts may be employed in this invention. In a preferred example of the process usually employed for this purpose, the amount introduced to the stabilizer and the amount withdrawn from the stabilizer are controlled by detecting the change of the liquid level of the contents of the oxidation reactor and the stabilizer by means of a level gage.

For example, a level gage is provided on each of the oxidation reactor and the stabilizer in such a manner that a control valve of a conduit for discharging the reaction product from the vessel is operated, i.e., the valve is fully opened or the opening of the valve is further increased when the liquid level of the reaction product in the vessel reaches the upper limit and the valve is fully closed or the opening of the valve is reduced when the liquid level of the content reached its lower limit. In this case, the upper limit and the lower limit of the liquid level in the oxidation reactor are set so that the amount of the oxidation reaction product withdrawn from the oxidation reactor and supplied to the stabilizer is kept below about 30% by volume of the contents of the stabilizer in a range so that continuous oxidation takes place smoothly. Also, in the stabilizer, the upper limit and the lower limit of the liquid level are set so that the amount of the reaction product withdrawn from the stabilizer is kept below about 30% by volume of the contents of the stabilizer in a range that the stabilization reaction takes place smoothly.

In another embodiment of maintaining the volume change of the contents of the stabilizer below about 30% by volume, the change of each liquid level in the oxidation reactor and the stabilizer is detected by means of a liquid gage provided on the oxidation reactor and the stabilizer, the change of volume of the contents of the oxidation reactor with the passage of time and the change of volume of the contents of the stabilizer are calculated by subjecting the signals thus detected to computor processing in a conventional manner, and both of the control valves for the conduit for withdrawing the contents of the oxidation reaction product from the oxidation reactor and the control valve for the conduit for withdrawing the reaction product from the stabilizer are controlled by such data so that the volume deviation of the contents of the stabilizer is kept below about 30% by volume.

In still another process, when the pressure in the oxidation reactor is almost the same as the pressure in the stabilizer, pumps capable of changing the amount of the product withdrawn from each vessel are employed in place of the control valve for the conduit for withdrawing the oxidation reaction product from the oxidation reactor and the control valve for the conduit for withdrawing the reaction product from the stabilizer, and the amount of the product withdrawn by each of the pumps is changed by the liquid level signal detected by each of the level gages of the oxidation reactor and the level gage of the stabilizer so as to control the volume change of the contents of the stabilizer below about 30% by volume.

A preferred embodiment of level gage is a gamma ray level gage. Other level gages may, of course, be used, but some of them frequently cause troubles in operation and reliability due to the presence of terephthalic acid crystals and corrosions by the solvent used.

An example of the embodiments of the present invention will then be illustrated in detail by referring to the accompanying drawing.

In the embodiment shown in the figure, an oxidation reactor 1 is equipped with a stirrer 2, a motor 3 for rotating the stirrer, a conduit 4 for introducing p-dialkylbenzene, solvent, and catalyst, a conduit 5 for introducing an oxygen containing gas, a conduit 6 for withdrawing the oxidation reaction product, a conduit 7 for discharging gas, a condenser 8, a receiver 9 for condensed liquid, a conduit 10 for refluxing the condensed liquid, and a conduit 11 for exhausting an off-gas. Also, a stabilizer 12 for subjecting the oxidation reaction product recovered from the oxidation reactor 1 to a stabilization treatment and a crystallization treatment is equipped with a stirrer 13, a motor 14 for rotating the stirrer, a conduit 15 for introducing an oxygen containing gas, a conduit 16 for introducing the off-gas exhausted from the oxidation reactor 1, a conduit 17 for withdrawing the reaction product, a conduit 18 for discharging gas, a condenser 19, a receiver 20 for condensed liquid, a conduit 21 for refluxing the condensed liquid, and a conduit 22 for exhausting gas.

Also, a gamma ray source 23a and a gamma ray detector 23b (level gage) are disposed so as to measure the liquid level, and the liquid level signal detected by the detector changes the opening of control valve 25 provided on the conduit 6 for withdrawing the oxidation reaction product through connection 24. The gamma ray source 23a and detector 23b and the control valve 25 are set in such a manner that the valve is fully opened or the opening of the valve is enlarged when the liquid level in the oxidation reactor 1 reaches the upper liquid level 26 and the valve is fully closed or the opening of the valve is reduced when the liquid level reaches the lower liquid level 27, whereby the oxidation reaction product is introduced continuously or intermittently into the stabilizer 12, as desired.

A gamma ray source 28a and a gamma ray detector 28b are also disposed with respect to the stabilizer 12 and the liquid level signal detected through connection 29 changes the opening of a control valve 30 provided in conduit 17 for withdrawing the reaction product. The level gages 28a and 28b and the control valve 30 are set in such a manner that the valve is fully opened or the opening of the valve is increased when the liquid level in the stabilizer 12 reaches the upper liquid level 31 and the valve is fully closed or the opening of the valve is reduced when the liquid level reaches the lower liquid level 32, and then the reaction product is withdrawn continuously or intermittently from the stabilizer 12.

For continuously producing high purity terephthalic acid using the apparatus shown in the figure, the desired amounts of p-dialkylbenzene, solvent and catalyst are continuously charged into the oxidation reactor 1 through conduit 4 and then an oxygen containing gas is continuously supplied in the reaction system through conduit 5 while stirring the reaction system by means of stirrer 2 to continuously oxidize the p-dialkylbenzene in the liquid phase. A gaseous mixture containing unreacted oxygen containing gas, evaporated solvent, steam formed, and unreacted raw material is withdrawn from conduit 7, cooled in condenser 8, introduced into receiver 9, and the uncondensed off-gas containing unreacted oxygen is exhausted from conduit 11 while the condensed liquid is refluxed to the reactor 1 through the conduit 10. When the reaction proceeds and the liquid level of the contents in the oxidation reactor 1 reaches the upper liquid level 26, the gamma ray level gage 23a and 23b generate a signal to open the control valve 25. Then, as the oxidation reaction product is withdrawn from the reactor 1, the liquid level reduces gradually, and when the liquid level reaches the lower liquid level 27, the level gage generates a signal to close the control valve.

The oxidation reaction product thus withdrawn from the oxidation reactor 1 is then introduced into stabilizer 12 through conduit 6. Then, while stirring the contents introduced in the stabilizer by means of stirrer 13, a predetermined amount of the off-gas from the oxidation reactor 1 is continuously supplied to stabilizer 12 through conduit 16 connected to conduit 11 and also a part of the oxygen containing gas supplied to the oxidation reactor 1 through conduit 5 is continuously supplied to the stabilizer 12 through conduit 15 connected to conduit 5 and conduit 16 in such a range that the oxygen concentration in the gas exhausted from exhaust gas conduit 22, that is, the oxygen concentration in the reaction system in the stabilizer, does not exceed the explosive limit. As the stabilization progresses, the liquid level in the stabilizer increases and when the liquid level reaches the upper liquid level 31, gamma ray level gage 28a and 28b generate a signal to open control valve 30. Then, as reaction product which has undergone stabilization with a retention time of about 5 to about 300 minutes is withdrawn from the stabilizer 12, the liquid level in the stabilizer gradually lowers, and when the liquid level in the stabilizer reaches the lower liquid level 32, the level gage generates a signal to close the control valve. The reaction product withdrawn from the stabilizer is sent to at least one crystallizer (not shown) through conduit 17. In addition, in the case of introducing the oxidation reaction product from oxidation reactor 1 to the stabilizer 12, level gage 23a and 23b of the oxidation reactor 1 are set beforehand in such a manner that the interval between the upper level 26 and the lower level 27 maintains the volume of the contents defined by the both liquid levels below about 30% by volume, preferably below 27% by volume, of the contents of the stabilizer. Thus, when the oxidation reaction product is intermittently withdrawn from the oxidation reactor 1, the amount of the oxidation product withdrawn each time is less than about 30% by volume, preferably less than 27% by volume, of the contents of the stabilizer. Furthermore, in the case of withdrawing the reaction product from the stabilizer 12, level gage 28a and 28b is set beforehand in such a manner that the interval between the upper liquid level 31 and the lower liquid level 32 maintains the volume of the contents defined by both liquid levels below about 30% by volume, preferably below 27% by volume, of the contents of the stabilizer.

As described above, according to the process of this invention, high purity terephthalic acid of constant quality can be obtained by only an oxidation reaction without any need for any additional purification treatments by introducing the oxidation reaction product obtained by the liquid phase oxidation of p-dialkylbenzene into a stabilizer and treating the oxidation reaction product therein with an off-gas, etc., having a low oxygen concentration, which is merely vented from the oxidation reactor in a conventional process, for extended periods of time while maintaining the volume change of the contents of the stabilizer below a definite level, whereby the materials to be oxidized contained in the oxidation reaction product are effectively subjected to stabilization continuously without the danger of explosion. Thus, the process of this invention is advantageous industrially.

As described above, according to the process of this invention, terephthalic acid of constant quality can be easily obtained, which is confirmed to have a purity of more than 99.9% by weight and a white color.

The invention will now be described in more detail by the following examples which should in no way be interpreted as limiting the scope of this invention.

EXAMPLE 1

The reactions were performed using a 40 liter titanium lined pressure oxidation reaction vessel equipped with a reflux condenser, a stirrer, heating means, an inlet for raw materials, an inlet for oxygen containing gas, an outlet for reaction product, and a gamma ray level gage; a 40 liter titanium lined stabilizer (also used as a 1st crystallizer) equipped with a reflux condenser, a stirrer, heating means, an inlet for the reaction product from the oxidation reaction vessel, an inlet for the off-gas from the oxidation reaction vessel and other oxygen containing gas, an outlet for reaction product, and a gamma ray level gage; and a 2nd crystallizer and 3rd crystallizer each having the same volume as that of the stabilizer, the apparatus generally being as shown in the figure except that crystallizers are not shown.

First, 12 kg of acetic acid, 61 g of cobalt acetate, 3 g of manganese acetate, and 36 g of sodium bromide were charged into the oxidation reactor, and, while maintaining the reaction system at a pressure of 20 kg/cm$^2$ and at a temperature of 190° C., air and p-xylene were introduced for 30 minutes at 4.2 NM$^3$/kg (p-xylene) and 2.4 kg/hr, respectively. While continuing the introduction of air and p-xylene, a catalyst acetic acid solution (the ratio and concentrations of cobalt acetate, manganese acetate, and sodium bromide were the same as those charged first in the reaction vessel) was introduced at a rate of 7.2 kg/hr to continuously perform the liquid phase oxidation reaction. On the other hand, about 11 kg of acetic acid was initially charged to the stabilizer (to avoid flashing, generally at process start-up a volatile material such as acetic acid is charged to the stabilizer to increase the pressure therein, whereafter the introduction of oxidation reaction product is begun) and thereafter the stabilizer maintained at a temperature of 180° C. and a pressure of 12 kg/cm$^2$, and then the level gage was set at a position which defined the interior volume below the upper liquid level to be 13.2 liters. During the progress of the oxidation reaction, the oxidation reaction product obtained in the oxidation reactor was introduced to the stabilizer intermittently and periodically at a time interval of 10 minutes and at a rate of 2.2 liters each time, according to the signal of the level gage of the oxidation reactor. At the same time that the introduction of the oxidation reaction product into the stabilizer is initiated, the off-gas and oxygen gas are introduced thereinto as described below.

Then, the off-gas containing 5% by volume unreacted oxygen from the oxidation reactor was continuously introduced into the stabilizer at a rate of 3.0 NM$^3$/hr, and, at the same time, air was also continuously introduced into the stabilizer at a rate of about 0.3 NM$^3$/hr so that the oxygen concentration in the off-gas became about 5%. The reaction product which had undergone stabilization was withdrawn from the stabilizer and introduced into the 2nd crystallizer. The mean retention time of the reaction product in the stabilizer was about 60 minutes and the volume change of the contents of the stabilizer during the stabilization was about 17%. The reaction product was treated in the 2nd crystallizer at a pressure of 7 kg/cm$^2$ and at a temperature of about 150° C. and a mean retention time of about 60 minutes and then in the 3rd crystallizer at normal pressure and at a temperature of about 115° C. and a mean retention time of about 60 minutes.

The aforesaid continuous production of terephthalic acid was continued for 5 hours, the reaction product withdrawn from the 3rd crystallizer was collected every hour, and the properties and the yield of terephthalic acid obtained by subjecting the reaction product to liquid-solid separation, washing, and drying were measured, the results being shown in Table 1.

It should be noted that oxygen gas is consumed during the stabilization, i.e., the off-gas contained 5% by volume of oxygen and additional oxygen was introduced, but the oxygen concentration of the off-gas in the stabilizer remained at 5%.

EXAMPLE 2

The same procedure as in Example 1 was followed except that the oxidation reaction product was continuously introduced from the oxidation reactor to the stabilizer at a rate of 13.2 liters/hr, the reaction product was continuously introduced from the stabilizer to the 2nd crystallizer at a rate of 13.2 liters/hr, the mean retention time of the reaction product in the stabilizer was about 60 minutes, and the volume change of the contents of the stabilizer was about 2%. The properties and the yield of terephthalic acid obtained are also shown in Table 1.

EXAMPLE 3

The same procedure as in Example 1 was followed except that the level gage was set at a position defining the contents of the stabilizer below the upper liquid level to be 8.8 liters, the volume change of the contents of the stabilizer was kept at about 25%, and the mean retention time of the reaction product in the stabilizer was about 40 minutes. The properties and the yield of terephthalic acid obtained are shown in Table 1.

EXAMPLE 4

The same procedure as in Example 1 was followed except that the level gage of the oxidation reactor was set in such a manner that the oxidation reaction product was introduced into the stabilizer intermittently and periodically at a time interval of 15 minutes and at a rate of 3.3 liters each time, and the level gage of the stabilizer was set at a position defining the contents of the stabilizer below the upper liquid level to 26.4 liters; the mean retention time of the reaction product in the stabilizer was about 120 minutes, and the volume change of the contents of the stabilizer was kept at about 12.5%. The properties and the yield of the terephthalic acid are shown in Table 1.

TABLE 1

| | Time of terephthalic acid collecting (hr) | Purity (wt %) | Content of 4-carboxy-benzaldehyde (ppm) | Molecular[1] extinction coefficient (E 380 mμ) | Color[2] diffence b-value | Mean yield (mol %) | Mean oxygen concentration in the stabilizer system (% by volume) |
|---|---|---|---|---|---|---|---|
| Example 1 | 1 | 99.97 | 290 | <0.01 | −0.1 | 96 | 5 |
| | 2 | " | 300 | " | −0.2 | | |
| | 3 | " | " | " | −0.1 | | |
| | 5 | " | 290 | " | " | | |
| Example 2 | 1 | 99.97 | 300 | <0.01 | −0.1 | 96 | 5 |
| | 2 | " | 290 | " | ±0 | | |
| | 3 | " | " | " | −0.1 | | |

TABLE 1-continued

|  | Time of terephthalic acid collecting (hr) | Purity (wt %) | Content of 4-carboxy-benzaldehyde (ppm) | Molecular[1] extinction coefficient (E 380 mµ) | Color[2] diffence b-value | Mean yield (mol %) | Mean oxygen concentration in the stabilizer system (% by volume) |
|---|---|---|---|---|---|---|---|
|  | 5 | " | 300 | " | −0.2 |  |  |
| Example 3 | 1 | 99.97 | 320 | <0.01 | ±0 | 96 | 5 |
|  | 2 | " | 300 | " | +0.1 |  |  |
|  | 3 | " | 320 | " | +0.2 |  |  |
|  | 5 | " | 310 | " | " |  |  |
| Example 4 | 1 | 99.97 | 280 | <0.01 | −0.2 | 96 | 5 |
|  | 2 | " | " | " | " |  |  |
|  | 3 | " | 270 | " | " |  |  |
|  | 5 | " | 280 | " | " |  |  |

[1]Absorption values at 380 mµ measured with the use of a spectrophotometer for a solution of 5 g of the terephthalic acid in 100 ml of 2N aqueous ammonia. The lower the value, the better the color.
[2]This value indicates the "apparent color" obtained by measuring reflected light from the terephthalic acid (solid) with the use of Color Machine CM-20, manufactured by Color Machine Co., all b-values indicating yellowness. The lower the value, the better being the color.

(1) Absorption values at 380 mµ measured with the use of a spectrophotometer for a solution of 5 g of the terephthalic acid in 100 ml of 2 N aqueous ammonia. The lower the value, the better the color. P (2) This value indicates the "apparent color" obtained by measuring reflected light from the terephthalic acid (solid) with the use of Color Machine CM-20, manufactured by Color Machine Co., all b-values indicating yellowness. The lower the value, the better being the color.

COMPARISON EXAMPLE 1

The same procedure as in Example 1 was followed except that only air was introduced into the stabilizer so that the oxygen concentration in the reaction system therein became 5% by volume and the off-gas from the oxidation reactor was not introduced into the stabilizer. The properties and the yield of terephthalic acid obtained are shown in Table 2.

In this comparison example, air having a high oxygen concentration was introduced into the stabilizer without being diluted with the off-gas and the stabilization carried out under conditions such that the oxygen concentration in the system did not exceed the explosive limit. Since air was blown into the reaction system without being diluted, the amount of air blown into the system was small, i.e., 0.23 NM³/hr, which resulted in reducing the dispersion effect of the oxygen, and thus uniform gas-liquid contact and a quick supply of oxygen were not obtained, which resulted in achieving insufficient stabilization. Therefore, the purity and color hue of terephthalic acid obtained were inferior to those of terephthalic acid obtained by the examples of this invention. Also, after about 3 hours from the initiation of the oxidation reaction, the conduit for introducing the reaction product from the stabilizer to the 2nd crystallizer clogged, and thus the operation had to be stopped.

COMPARISON EXAMPLE 2

The same procedure as in Example 1 was followed except that only air was introduced into the stabilizer at a rate of 0.85 NM³/hr and the off-gas from the oxidation reactor was not introduced therein. The properties and yield of terephthalic acid obtained are shown in Table 2.

In this comparison example, since the amount of air was increased, the dispersing effect of oxygen was increased and since uniform gas-liquid contact and quick supply of oxygen were obtained, the properties and yield of terephthalic acid formed were improved. However, in this case the oxygen concentration in the stabilizer became 16%, which exceeded the explosive limit, and hence operation was stopped 3 hours after the initiation of the oxidation reaction.

COMPARISON EXAMPLE 3

The same procedure as in Example 1 was followed except that air and the off-gas from the oxidation reactor were not introduced into the stabilizer. The properties and yield of terephthalic acid obtained are shown in Table 2.

In this comparison example, stabilization was not performed in the stabilizer, and, hence, the purity and color hue of the terephthalic acid were lower than those in the examples of this invention. Also, the conduit for introducing the reaction product from the stabilizer to the 2nd crystallizer clogged about 3 hours after the initiation of the oxidation reaction, and thus operation was stopped.

COMPARISON EXAMPLE 4

The same procedure as in Example 1 was followed except that the level gage of the oxidation reactor was set in such a manner that the oxidation reaction product was introduced into the stabilizer intermittently and periodically at an interval of 45 seconds and at a rate of 0.165 liter each time; also, the level gage of the stabilizer was set at a position defining the contents of the stabilizer below the upper liquid level to 0.7 liter; the mean retention time of the reaction product was about 3 minutes; and the volume deviation of the contents of the stabilizer was kept at about 24%. The properties and yield of terephthalic acid obtained are shown in Table 2.

In this comparison example, a sufficient stabilization effect was not obtained due to the short retention time of the reaction product in the stabilizer, and, therefore, the purity and color hue of the terephthalic acid obtained were lower than those of terephthalic acid obtained in the examples of this invention.

COMPARISON EXAMPLE 5

The same procedure as in Example 1 was followed except that the level gage of the oxidation reactor was set in such a manner that the oxidation reaction product was introduced into the stabilizer intermittently and periodically at a time interval of 25 minutes and a rate of 5.5 liters each time, and the volume change of the contents of the stabilizer was maintained at about 42%. The properties and yield of terephthalic acid obtained are shown in Table 2.

In this comparison example, the control of temperature and pressure of the reaction system was difficult due to the large volume change of the contents of the stabilizer, and thus the quality of terephthalic acid obtained changed and a product having constant properties was not obtained.

below about 27% by volume, by controlling the amount of the oxidation reaction product introduced from the oxidation reactor to the stabilizer and the amount of the oxidation reaction product discharged from the stabilizer, thereby to maintain the volume change of the contents below about 27% by volume.

2. The process as claimed in claim 1 wherein acetic acid is used as the solvent.

TABLE 2

|  | Time of terephthalic acid collecting (hr) | Purity (wt %) | Content of 4-carboxy-benzaldehyde (ppm) | Molecular[1] extinction coefficient (E 380 mμ) | Color[2] diffence b-value | Mean yield (mol %) | Mean oxygen concentration in the stabilizer system (% by volume) |
|---|---|---|---|---|---|---|---|
| Comparison Example 1 | 1 | 99.95 | 390 | 0.02 | +0.7 | 93 | 5 |
|  | 2 | " | 400 | " | +0.8 |  |  |
|  | 3 | " | 410 | " | +0.9 |  |  |
| Comparison Example 2 | 1 | 99.97 | 290 | <0.01 | −0.2 | 96 | 16 |
|  | 2 | " | " | " | −0.1 |  |  |
|  | 3 | " | 300 | " | −0.2 |  |  |
| Comparison Example 3 | 1 | 99.93 | 600 | 0.05 | +1.9 | 91 | — |
|  | 2 | " | 590 | " | +2.0 |  |  |
|  | 3 | " | " | " | +1.9 |  |  |
| Comparison Example 4 | 1 | 99.95 | 370 | 0.02 | +0.8 | 93 | 5 |
|  | 2 | " | 380 | " | +0.9 |  |  |
|  | 3 | " | " | " | " |  |  |
|  | 5 | " | 370 | " | +0.7 |  |  |
| Comparison Example 5 | 1 | 99.97 | 300 | <0.01 | ±0 | 95 | 5 |
|  | 2 | 99.96 | 330 | 0.02 | +0.6 |  |  |
|  | 3 | 99.95 | 370 | " | +0.8 |  |  |
|  | 4 | 99.97 | 280 | <0.01 | +0.1 |  |  |
|  | 5 | 99.95 | 380 | 0.02 | +1.1 |  |  |

Note:
[1] and [2] are the same as in Table 1.

While the invention has been described in detail and with reference to specific embodiments thereof, it will be apparent to one skilled in the art that various changes and modifications can be made therein without departing from the spirit and scope thereof.

What is claimed is:

1. In a process of continuously producing high purity terephthalic acid by continuously introducing one or more p-dialkylbenzenes into an oxidation reactor together with a solvent and an oxidation catalyst, subjecting the raw material to a liquid phase oxidation with molecular oxygen or molecular oxygen containing gas, and separating and recovering terephthalic acid formed from the reaction mixture, the improvement which comprises continuously or intermittently introducing the oxidation reaction product from the oxidation reactor into a stabilizer which can retain the oxidation reaction product from the oxidation reactor for 10 to 200 minutes and also can keep the volume change of the contents below 27% by volume even while oxidation reaction product is being introduced and oxidatively treating the oxidation reaction product in the stabilizer, to completely oxidize oxidizable materials selected from the group consisting of unreacted feed materials, reaction intermediate products and active compounds, for about 10 to 200 minutes at a temperature and pressure the same as or lower than those employed in the preceding oxidation reaction by continuously introducing a molecular oxygen containing gas selected from the group consisting of an off-gas exhausted from the oxidation reactor and a mixture thereof with air, said molecular oxygen containing gas having an oxygen concentration of 2 to 15 volume % so that the oxygen concentration in the reaction system does not exceed the explosive limit during said treatment and while maintaining the volume change of the contents in the stabilizer below about 27% by volume, by controlling the amount of the oxidation reaction product introduced from the oxidation reactor to the stabilizer and the amount of the oxidation reaction product discharged from the stabilizer, thereby to maintain the volume change of the contents below about 27% by volume.

2. The process as claimed in claim 1 wherein acetic acid is used as the solvent.

3. The process as claimed in claim 1 wherein the solvent is used in an amount of about 2 to about 6 times by weight the amount of the one or more p-alkylbenzenes.

4. The process as claimed in claim 1 wherein a catalyst containing cobalt, manganese and bromine is used as the oxidation catalyst.

5. The process as claimed in claim 1 wherein air is used as the molecular oxygen containing gas introduced into the oxidation reactor.

6. The process as claimed in claim 1 wherein the p-dialkylbenzene is p-xylene.

7. The process as claimed in claim 1 wherein the liquid phase oxidation reaction in the oxidation reactor is carried out at temperatures of about 80° to about 250° C. and at pressures of about 2 to about 30 kg/cm² gauge.

8. The process as claimed in claim 1 wherein the mean retention time of the reactants in the oxidation reactor is about 0.5 to about 6 hours.

9. The process as claimed in claim 1 wherein the oxygen concentration of the molecular oxygen containing gas to be introduced into the stabilizer is about 2 to about 15% by volume.

10. The process as claimed in claim 1 wherein the oxidation treatment in the stabilizer is carried out at temperatures lower than the temperature in the main oxidation reaction by 0° to 100° C. and at pressures of about 2 to about 30 kg/cm² gauge.

11. The process as claimed in claim 1 wherein the mean retention time of the reactant in the stabilizer is 10 to 200 minutes.

12. The process as claimed in claim 1 wherein the contents of the stabilizer is substantially the same as that of the oxidation reactor.

13. The process as claimed in claim 1 wherein crystallization of terephthalic acid and the oxidation of materials to be oxidized contained in the oxidation reaction product are carried out in the stabilizer.

14. The process as claimed in claim 13 wherein the materials to be oxidized are reaction intermediate products and active compounds.

15. The process as claimed in claim 1 wherein the amount of the off-gas from the oxidation reactor introduced into the stabilizer is about 0.01 to about 10,000 liters per kilogram of oxidation reaction product.

16. The process as claimed in claim 1 wherein the amount of the off-gas from the oxidation reactor introduced into the stabilizer is about 0.01 to about 10,000 liters per kilogram of oxidation reaction product and the amount of air introudced is less than about 2,000 liters per kilogram of the oxidation reaction product.

17. The process as claimed in claim 1 wherein the reaction product from the stabilizer is introduced into at least one crystallizer to complete the crystallization thereof therein and then solid terephthalic acid is separated by means of solid-liquid separation and dried.

* * * * *